United States Patent
Romo et al.

(10) Patent No.: US 10,143,268 B2
(45) Date of Patent: Dec. 4, 2018

(54) ACHILLES HEEL WEDGE

(71) Applicant: OSSUR HF, Reykjavik (IS)

(72) Inventors: Harry Duane Romo, Aliso Viejo, CA (US); Jonathan Walborn, Mission Viejo, CA (US); Larus Gunnsteinsson, Reykjavik (IS)

(73) Assignee: OSSUR HF, Reykjavik (IS)

(*) Notice: Subject to any disclaimer, the term of this patent is extended or adjusted under 35 U.S.C. 154(b) by 213 days.

(21) Appl. No.: 14/803,351

(22) Filed: Jul. 20, 2015

(65) Prior Publication Data

US 2016/0015121 A1 Jan. 21, 2016

Related U.S. Application Data

(60) Provisional application No. 62/026,884, filed on Jul. 21, 2014.

(51) Int. Cl.
*A43B 7/16* (2006.01)
*A43B 7/14* (2006.01)
(Continued)

(52) U.S. Cl.
CPC .......... *A43B 17/023* (2013.01); *A43B 7/144* (2013.01); *A43B 17/006* (2013.01); *A61F 5/0111* (2013.01); *A61F 5/0127* (2013.01)

(58) Field of Classification Search
CPC ......... A43B 7/16; A43B 7/144; A43B 7/1465; A43B 17/02; A43B 17/023; A43B 17/006
(Continued)

(56) References Cited

U.S. PATENT DOCUMENTS 1,674,687 A 6/1928 McCormick
2,184,209 A 12/1939 Burger
(Continued)

FOREIGN PATENT DOCUMENTS

DE 35 20 714 A1 12/1986
DE 93 14 920 U1 3/1994
(Continued)

OTHER PUBLICATIONS

"Bledsoe Achilles Boot Rise Kit, Application Instructions, Total Leg Support System with Infinite R.O.M. and Short Application Time," Council Directive 93/42/EEC of Jun. 14, 1993 concerning Medical Devices. http://www.bledsoebrace.com/products/achilles-boot/.
(Continued)

*Primary Examiner* — Jameson Collier
*Assistant Examiner* — Heather Mangine
(74) *Attorney, Agent, or Firm* — Workman Nydegger

(57) ABSTRACT

An Achilles heel wedge has a front part, a back part, and a longitudinal axis extending in a longitudinal direction between the front part and the back part. A first wedge section defines a bottom surface and a top surface. The top surface of the first wedge section forms a convex portion curving along the longitudinal axis and extending between side portions of the first wedge section. The convex portion is positionable under the longitudinal arch of a user's foot during use. A second wedge section is removably attachable to the bottom surface of the first wedge section. The second wedge section defines substantially parallel top and bottom surfaces and a ramped edge at or near a front of the second wedge section. The ramped edge extends downwardly and forwardly relative to the first wedge section and the top surface of the second wedge section.

10 Claims, 8 Drawing Sheets

(51) Int. Cl.
*A43B 17/02* (2006.01)
*A43B 17/00* (2006.01)
*A61F 5/01* (2006.01)

(58) Field of Classification Search
USPC .............. 36/92, 81, 181, 173, 150, 155, 159
See application file for complete search history.

(56) References Cited

U.S. PATENT DOCUMENTS

| | | | |
|---|---|---|---|
| 2,212,414 | A | 8/1940 | Burger |
| 2,509,423 | A | 5/1950 | Cramer |
| 2,700,230 | A | 1/1955 | Beyer |
| 3,124,887 | A | 3/1964 | Vassar |
| 4,223,455 | A | 9/1980 | Vermeulen |
| 4,942,677 | A | 7/1990 | Flemming et al. |
| 4,955,370 | A | 9/1990 | Pettine |
| 5,078,128 | A | 1/1992 | Grim et al. |
| 5,133,776 | A | 7/1992 | Crowder |
| 5,138,774 | A * | 8/1992 | Sarkozi ................. A43B 7/14 36/159 |
| 5,152,081 | A | 10/1992 | Hallenbeck et al. |
| 5,329,705 | A | 7/1994 | Grim et al. |
| 5,399,152 | A | 3/1995 | Habermeyer et al. |
| 5,437,111 | A | 8/1995 | Kousaka et al. |
| 5,464,385 | A | 11/1995 | Grim |
| 5,732,481 | A | 3/1998 | Farhad |
| 5,782,015 | A | 7/1998 | Danaberg |
| 5,902,259 | A | 5/1999 | Wilkerson |
| 5,954,075 | A | 9/1999 | Gilmour |
| 6,503,178 | B1 | 1/2003 | Gibbons |
| D483,556 | S | 12/2003 | Zehr |
| 6,755,798 | B2 | 6/2004 | McCarthy et al. |
| 6,984,197 | B2 | 1/2006 | Sugiyama et al. |
| 7,198,610 | B2 | 4/2007 | Ingimundarson et al. |
| 7,303,538 | B2 | 12/2007 | Grim et al. |
| 8,313,451 | B2 | 11/2012 | Cox |
| 2001/0000369 | A1 * | 4/2001 | Snyder ................. A43B 7/1495 36/44 |
| 2003/0226288 | A1 * | 12/2003 | Brown ................... A43B 7/141 36/144 |
| 2004/0019307 | A1 | 1/2004 | Grim et al. |
| 2004/0259704 | A1 | 12/2004 | Liang |
| 2005/0131324 | A1 | 6/2005 | Bledsoe |
| 2005/0267603 | A1 | 12/2005 | Lecomte et al. |
| 2007/0204487 | A1 | 9/2007 | Clough |
| 2009/0287127 | A1 | 11/2009 | Hu et al. |
| 2010/0042032 | A1 | 2/2010 | Tomczak |
| 2010/0331749 | A1 | 12/2010 | Powaser |
| 2011/0021963 | A1 | 1/2011 | Graddon et al. |
| 2011/0087142 | A1 | 4/2011 | Ravikumar et al. |
| 2012/0000092 | A1 | 1/2012 | Ingvarsson et al. |
| 2012/0035520 | A1 | 2/2012 | Ingimundarson et al. |
| 2013/0310721 | A1 | 11/2013 | Hu et al. |

FOREIGN PATENT DOCUMENTS

| | | |
|---|---|---|
| DE | 10 319 480 A1 | 11/2004 |
| EP | 0 409 101 A2 | 1/1991 |
| FR | 3044524 A1 * | 6/2017 .............. A43B 7/144 |
| GB | 2 367 763 A | 4/2002 |
| GB | 2429394 A * | 2/2007 .............. A43B 7/16 |
| JP | H 07-184968 A | 7/1995 |
| WO | WO 92/04880 A1 | 4/1992 |
| WO | WO 2004/009001 A1 | 1/2004 |

OTHER PUBLICATIONS

"This Boot is Made for Walking," The Rebound Air Walker by Ossur, Life Without Limitations, http://ww.ossur.com/lisalib/getfile.aspx?itemid+20244, 2010.

International Search Report from corresponding International PCT Application No. PCT/US2015/041089, dated Oct. 5, 2015.

International Search Report from corresponding International PCT Application No. PCT/US2015/044434, dated Oct. 8, 2015.

* cited by examiner

ACHILLES HEEL WEDGE

TECHNICAL FIELD

The disclosure relates to an Achilles heel wedge for use in the treatment, repair, and rehabilitation of the Achilles tendon.

BACKGROUND

Achilles tendon rupture is the most common injury involving a tear in a tendon. It commonly occurs as a sports injury during explosive acceleration, for example, while pushing off or jumping up.

Treatment of Achilles tendon rupture is typically divided between operative and non-operative management, each of which involve holding the foot in a plantar-flexed position and then gradually lengthening (stretching) the tendon as it heals and strengthens.

Operative management involves a surgical operation where the ruptured tendon is sutured back together at the point of rupture, and the leg is then placed into a cast. When the leg is placed in the cast, the foot is pointed downward (in an equinus position). As the healing progresses, the equinus position is then gradually decreased (requiring removal of the original cast, and recasting with the newly decreased equinus position).

Non-operative management typically involves wearing a cast or walking boot, which allows the ends of the torn tendon to reattach themselves on their own. In the non-operative option, the foot is pointed downwards, with the help of heel wedges or insoles, which are placed in the walker boot or cast. The height of the heel wedges or insoles is then incrementally decreased as the process of healing progresses.

Studies have shown that patients have quicker and more successful recoveries when they are allowed to move and lightly stretch their ankle immediately after surgery. To keep their ankle safe while healing, these patients can use a removable boot while walking and/or doing daily activities.

In either the operative or non-operative situation, existing methods for repairing the Achilles tendon can cause unwanted changes in stretching the length of the Achilles tendon, such that the risk of re-rupture of the tendon is increased. Additionally, existing methods for Achilles tendon repair can be inconvenient and uncomfortable to implement. For instance, the fit between conventional Achilles heel wedges and the foot tends to be rather unnatural, causing the user to feel unstable and apply additional and possibly harmful stress on the foot. Conventional Achilles heel wedges also lack overall usability, including a lack of consistency in the heel and foot position.

SUMMARY

The disclosure describes various embodiments of an Achilles heel wedge providing a construction and design that facilitates more comfortable and natural support of a user's foot during the treatment, repair, and/or rehabilitation of the Achilles tendon.

The embodiments described can include an Achilles heel wedge having a front part, a back part, and a longitudinal axis extending in a longitudinal direction between the front part and the back part.

A first wedge section defines a bottom surface and a top surface. The top surface of the first wedge section forms a convex portion curving along the longitudinal axis and extending between side portions of the first wedge section. The convex portion is positionable under the longitudinal arch of a user's foot. The longitudinal arch of the user's foot can include the longitudinal arch on the medial side of the user's foot (e.g., medial arch) and/or the longitudinal arch on the lateral side of the user's foot (e.g., lateral arch).

A second wedge section is removably attachable to the bottom surface of the first wedge section. The second wedge section defines substantially parallel top and bottom surfaces and a ramped edge at or near a front of the second wedge section. The ramped edge extends downwardly and forwardly relative to the first wedge section and the top surface of the second wedge section.

The curvature and location of the convex portion advantageously increases user comfort by improving the fit between the Achilles heel wedge and the natural curve of the foot rather than providing only an angled ramped shape, as in the prior art. The convex portion can further relieve pain and take pressure off of the foot and the ligaments and tendon that support the foot.

The convex portion can also increase user comfort by reducing pressure points or pressure lines along the plantar surface of the foot. For instance, the convex portion can distribute pressure away and/or throughout the lateral arch of the foot rather than overloading or concentrating pressure on one or more areas of the lateral arch via a discrete straight edge as in the prior art.

The configuration and dimensioning of the convex portion can also help the Achilles heel wedge support the user's medial arch without the need of a separate or dedicated arch support. For instance, where a user has flat feet, the curvature of the convex portion can contact and support the user's medial arch in an equinus position or the plantar-flexed position, taking pressure off the medial arch.

According to a variation, the first wedge portion includes a ramped edge extending downwardly and forwardly from the convex portion. The ramped edges of the first and second wedge portions in combination approximate the curvature of the convex portion. This advantageously helps form a long, smooth curve-like shape along the top of the Achilles heel wedge, improving the fit and comfort of the Achilles heel wedge.

According to a variation, a separate arch support is attachable to an upper surface of the Achilles heel wedge. The arch support has a contoured, elongate configuration extending substantially between the heel and forefoot of the user. This helps maintain the position of the user's heel or calcaneus on the Achilles heel wedge, reducing the likelihood of the foot undesirably shifting or moving during use of the Achilles heel wedge.

Additional features and advantages of embodiments of the present disclosure will be set forth in the description that follows, and in part will be obvious from the description, or may be learned by the practice of such exemplary embodiments. These and other features will become more fully apparent from the following description and appended claims, or may be learned by the practice of such exemplary embodiments as set forth hereinafter.

BRIEF DESCRIPTION OF THE DRAWINGS

To further clarify the above and other advantages and features of the present disclosure, a more particular description of the disclosure will be rendered by reference to specific embodiments illustrated in the drawings. It is appreciated that these drawings depict only typical embodiments of the disclosure and are not to be considered limiting of scope, and are not necessarily drawn to scale. The disclosure will be described and explained with additional specificity and detail through the use of the accompanying drawings.

DETAILED DESCRIPTION

Figure 1:
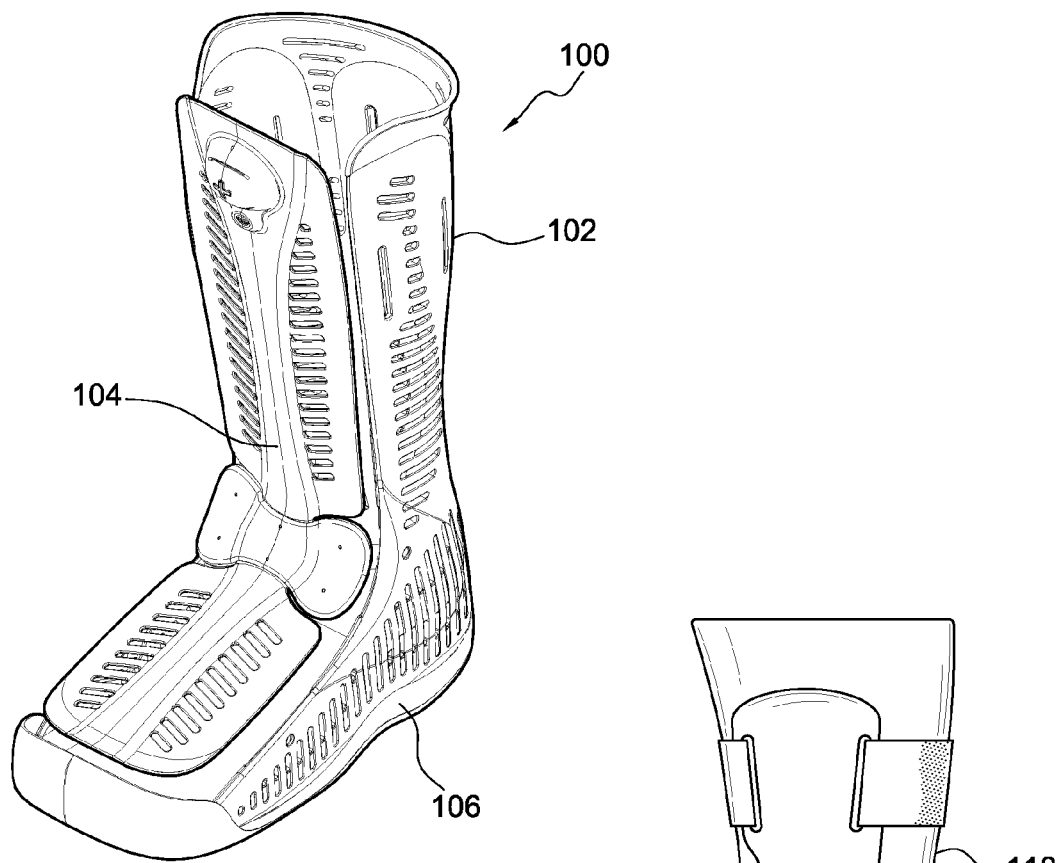
FIG. 1 is an isometric view of circumferential type walking boot (walker) in which the exemplary embodiments of an Achilles heel wedge may be implemented.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

It will be understood that, unless a term is expressly defined in this disclosure to possess a described meaning, there is no intent to limit the meaning of such term, either expressly or indirectly, beyond its plain or ordinary meaning.

Exemplary embodiments of an Achilles heel wedge are provided for use in the treatment, repair, and rehabilitation of the Achilles tendon following an injury and/or corrective surgery. Features that are provided on one side of the wedge can easily be provided on the other side of the wedge. In this manner, it is intended that the exemplary embodiments of the Achilles heel wedge described herein may be used on either right or left lower legs, with any appropriate reconfiguration of components that is deemed necessary for the proper fit and function of the wedge for the purpose of treatment, repair, and rehabilitation of the Achilles tendon of either the left or right lower leg.

The exemplary embodiments of the disclosure are adapted for treatment, repair, and rehabilitation of the Achilles tendon of human beings, and may be dimensioned to accommodate different types, shapes and sizes of human joints and appendages.

The exemplary embodiments of an Achilles heel wedge can be implemented in various orthopedic devices, including, but not limited to, configurations of walking boots, orthopedic shoes, or post-surgical shoes.

For example, exemplary embodiments of an Achilles heel wedge can be implemented within a circumferential type walker 100, as shown in FIG. 1. An exemplary circumferential type walker 100 includes a base shell 102 and a dorsal shell or plate 104, such that the lower leg is generally fully enclosed and supported by the walker 100. An outsole 106 is provided along the distal plantar surface of the walker 100.

Figure 2:
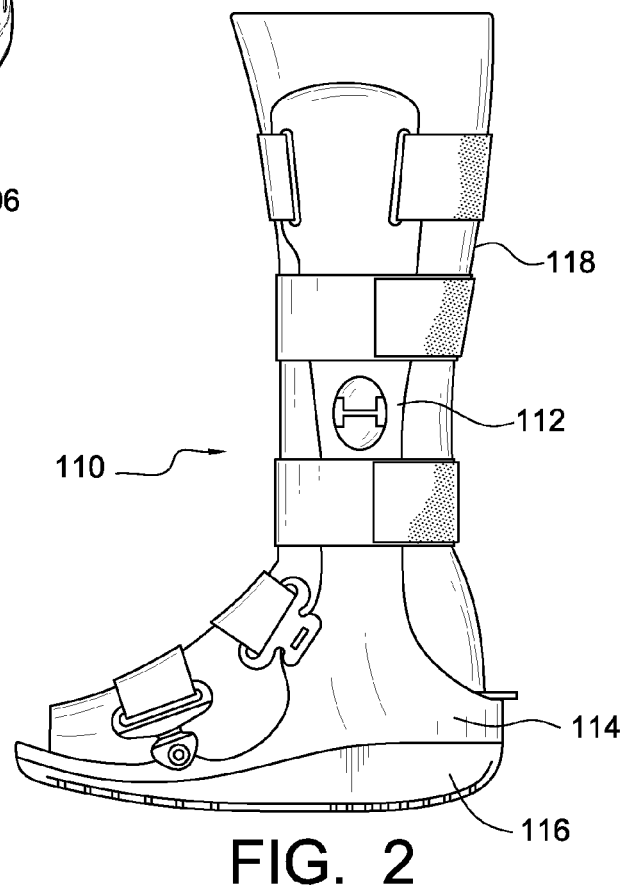
FIG. 2 is a side view of another type of walker in which the exemplary embodiments of an Achilles heel wedge may be implemented.

Further, exemplary embodiments of an Achilles heel wedge can be implemented within a walker 110, as shown in FIG. 2. The walker 110 includes a sole portion 114 having supporting struts 112 extending therefrom, and an outsole 116. A liner 118 can be provided enclosing the lower leg and positioned between, and supported, by the supporting struts 112.

For further ease of understanding the exemplary embodiments as disclosed herein, a description of a few terms is necessary. As used herein, the term "dorsal" has its ordinary meaning and refers to the top surfaces of the foot, ankle and foreleg or shin. As used herein, the term "plantar" has its ordinary meaning and refers to a bottom surface, such as the bottom of a foot. As used herein, the term "proximal" has its ordinary meaning and refers to a location that is closer to the heart than another location. Likewise, the term "distal" has its ordinary meaning and refers to a location that is further from the heart than another location. The term "posterior" also has its ordinary meaning and refers to a location that is behind or to the rear of another location. Lastly, the term "anterior" has its ordinary meaning and refers to a location that is ahead of or to the front of another location.

The terms "rigid," "flexible," and "resilient" may be used herein to distinguish characteristics of portions of certain features of the orthopedic device. The term "rigid" is intended to denote that an element of the device is generally devoid of flexibility. Within the context of support members or shells that are "rigid," it is intended to indicate that they do not lose their overall shape when force is applied, and in fact they may break if bent with sufficient force. On the other hand, the term "flexible" is intended to denote that features are capable of repeated bending such that the features may be bent into retained shapes or the features do not retain a general shape, but continuously deform when force is applied. The term "resilient" is used to qualify such flexible features as generally returning to an initial general shape without permanent deformation. As for the term "semi-rigid," this term is used to denote properties of support members or shells that provide support and are free-standing; however such support members or shells may have some degree of flexibility or resiliency.

A first exemplary embodiment of an Achilles heel wedge comprises an Achilles heel wedge 200 having a plurality of wedge sections 252, 254, 256. The wedge sections can be attached to one another and selectively removable from the Achilles heel wedge 200 to customize the height of the Achilles heel wedge 200 as needed. The Achilles heel wedge 200 defines a longitudinal axis A-A extending between a back part 292 and a front part 294 of the Achilles heel wedge 200.

The wedge sections 252 254, 256 can be secured together with double sided tape. Alternatively, the wedge sections 252, 254, 256 can be secured together with adhesives, hook and loop type systems, a post inserted in a corresponding hole, frictional forces, combinations thereof, or any other appropriate technique. The wedge section 252 can be longer than the wedge section 254 and the wedge section 254 can be longer than the wedge section 256.

One or more of the wedge sections 252, 254, 256 can be formed by one or more materials providing a lightweight, supportive construction of the Achilles heel wedge 200. One or more of the wedge sections 252, 254, 256 can be formed from ethylene-vinyl acetate ("EVA") foam. For instance, at least one of the wedge sections 252, 254, 256 can be formed from medium-weight EVA foam (e.g., a 12-14 # EVA foam) to provide light-weight cushioning without compressing over time when used by a user weighing up to about 300 pounds. This can also allow the Achilles heel wedge 200 to perform consistently over a range of environmental conditions. The Achilles heel wedge 200 can be made from compression molded EVA foam.

Another suitable material may be an EVA cork mixture that is thermo moldable at approximately 120 to 140 degrees and results in a density/hardness of about between about 15 and about 90 shore, about 30 and about 80 shore, or about 40 and about 60 shore. Other suitable materials may be an artificial cork, elastomers, rubber, vinyl nitrile foam, polyurethane foam, combinations thereof, or any other suitable material. For instance, one or more of the wedge sections 252, 254, 256 can be formed from a #14 polyethylene foam with a hardness of between about 40 and 50 shore A.

Figure 3:
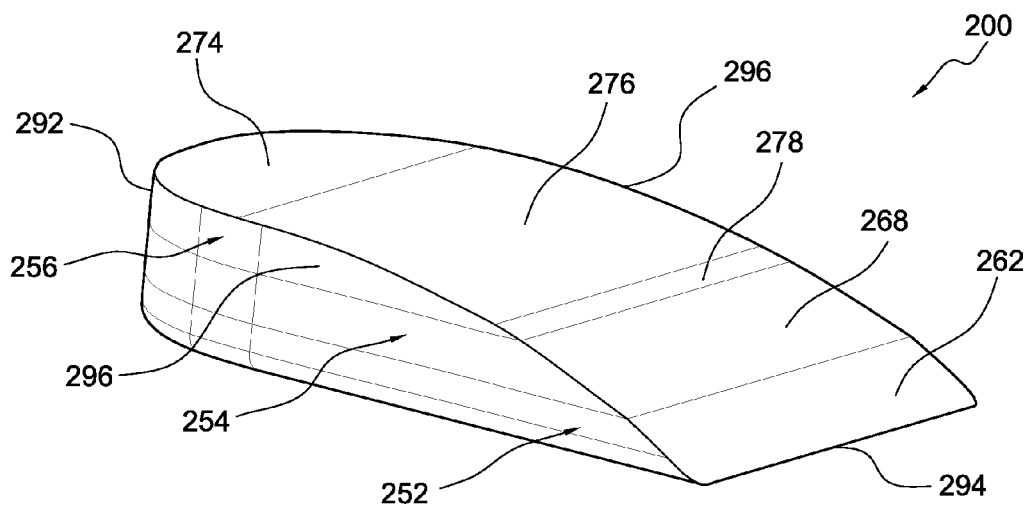
FIG. 3 is an isometric view of an Achilles heel wedge according to an embodiment.
Figure 4:
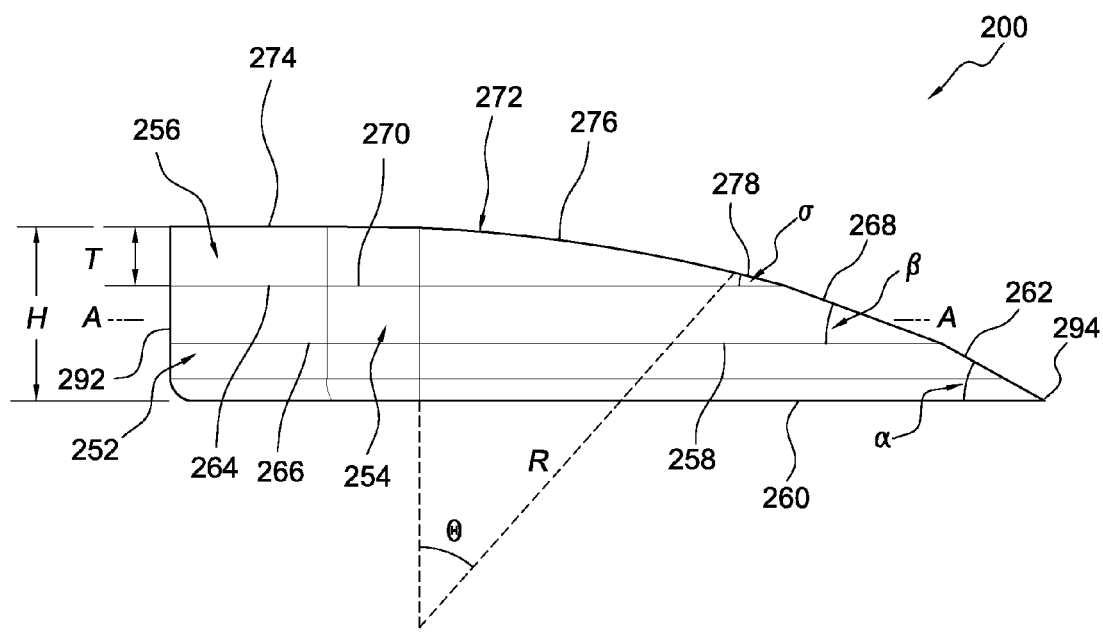
FIG. 4 is side view of the Achilles heel wedge shown in FIG. 3.

As seen in FIGS. 3 and 4, the lower or third wedge section 252 can include generally or substantially parallel top and bottom surfaces 258, 260 with a ramped edge 262 at or near a front of the wedge section 252. The ramped edge 262 can have a chamfered and/or beveled configuration. The ramped edge 262 can include one or more portions curving along the longitudinal axis A-A. The ramped edge 262 can generally face the toes of the user. The ramped edge 262 can be sized and configured to be positioned slightly proximal of the metatarsal heads on the forefoot or in any other suitable location. The ramped edge 262 can extend at an angle α between the top surface 258 and the bottom surface 260. The ramped edge 262 can extend at a higher angle than the other ramped edges discussed below, which, in turn, can create a shorter ramp. The angle α can be between about 15 degrees and about 45 degrees (e.g., about 30 degrees) relative to horizontal. It will be appreciated that the angle α can be greater or less depending on the number and/or construction of the wedge sections, the desired treatment protocol, and/or other requirements.

The top and bottom surfaces 258, 260 can be generally level or planar. The bottom surface 260 can define a bottom of the Achilles heel wedge 200 and can be arranged to interface with a support surface. The wedge section 252 can include generally parallel medial and lateral side portions, and curved posterior side portion. The side portions of the wedge section 252 can be angled relative to another. For instance, a width of the wedge section 252 defined between the side portions can taper from the back part 292 to the front part 294 of the Achilles heel wedge 200. Optionally, the wedge section 252 can include radii on one or more of the bottom edges.

The second or intermediate wedge section 254 can be situated on the top surface 258 of the wedge section 252. As seen, the wedge section 254 can be shorter than the wedge section 252. The wedge section 254 can include generally or substantially parallel top and bottom surfaces 264, 266 with a ramped edge 268 at or near a front of the wedge section 254. The ramped edge 268 can have a chamfered or beveled configuration. The ramped edge 268 can be angled relative to the top surface 258. One or more portions of the ramped edge 268 can curve along the longitudinal axis A-A. The ramped edge 268 can generally face the toes of the user.

In the illustrated embodiment, the ramped edge 262 of the wedge section 252 can extend downwardly and forwardly from the ramped edge 268 toward the bottom surface 260. The ramped edge 268 can extend at an angle β between the top surface 264 and the bottom surface 266. The angle β can be less than the angle α of the ramped edge 262, which, in turn, can result in a ramp length that is longer than the ramped edge 262. The angle β can be between about 10 degrees and about 30 degrees (e.g., about 20 degrees) relative to horizontal. It will be appreciated that the angle β can be greater or less depending on the number and/or construction of the wedge sections, the desired treatment protocol, and/or other requirements.

The top and bottom surfaces 264, 266 can be generally level or generally planar. The bottom surface 266 can be removably attached to the top surface 258 of the wedge section 252. When the wedge section 252 is removed from the Achilles heel wedge 200, the bottom surface 266 of the wedge section 254 can define a bottom of the Achilles heel wedge 200 and can be arranged to interface with a plantar support surface of the orthopedic device. Similar to the wedge section 252, the wedge section 254 can include generally parallel medial and lateral side portions, and a curved posterior side portion. The side portions of the wedge section 254 can be angled relative to another. For instance, a width of the wedge section 254 defined between the side portions can taper from the back part 292 to the front part 294 of the Achilles heel wedge 200. The wedge section 254 can further include radii on one or more of the bottom edges.

The wedge section 256 can be the first or topmost wedge section situated on the top surface 264 of the wedge section 254. As seen, the wedge section 256 can be shorter than the wedge section 254 and can taper from back to front or heel to toe. The wedge section 256 can include a generally level bottom surface 270 and a top surface 272. Optionally, the wedge section 246 can include one or more heat formable materials to generally shape the top surface 272 of the wedge section 256 to the plantar surface of the foot.

The bottom surface 270 can be removably attached to the top surface 264 of the wedge section 254. When the wedge sections 252, 254 are removed from the Achilles heel wedge 200, the bottom surface 270 can define a bottom of the Achilles heel wedge 200 and can be arranged to interface with the support surface. The wedge section 256 can include generally parallel medial and lateral side portions 296, and a curved posterior side portion. The side portions 296 of the wedge section 256 can be angled relative to another. For instance, a width of the wedge section 252 defined between the side portions 296 can taper from the back part 292 to the front part 294 of the Achilles heel wedge 200. Optionally radii on the bottom edges similar to the wedge section 252.

The top surface 272 can include a substantially level or planar portion 274 and a convex portion 276 curving along the longitudinal axis A-A and at least in part between the back and front parts 292, 294 of the Achilles heel wedge 200. The convex portion 276 can extend from the planar portion 274 toward the mid-foot region and/or forefoot region of the user's foot and/or Achilles heel wedge 200. The convex portion 276 can extend forwardly beyond the user's heel or heel region. The convex portion 276 can extend between the side portions 296 of the wedge section 256. The convex portion 276 can extend only a portion of or the entire distance between the side portions 296 of the wedge section 256. Alternatively, the planar portion 274 can be omitted and the convex portion 276 can extend downwardly and forwardly from substantially the back part 292 of the Achilles heel wedge 200. Optionally, the planar portion 274 and/or the convex portion 276 can define a heel cup. For instance, the heel cup can be a concave feature defined in the top surface of the planar portion 274.

Generally, the curvature and location of the convex portion 276 increases user comfort by improving the fit between the Achilles heel wedge 200 and the natural curvature of the plantar surface of the foot rather than providing only an angled ramped shape, as in the prior art. For instance, the convex portion 276 can be configured and dimensioned to be situated under the natural curve or longitudinal arch of a user's foot during use. As noted above, the longitudinal arch can include the longitudinal arch on the medial side of the user's foot (e.g., medial arch) and/or the longitudinal arch on the lateral side of the user's foot (e.g., lateral arch). The convex portion 276 within the longitudinal arch of the foot can beneficially relieve pain and take pressure off of the foot and the ligaments and tendon that support the foot.

It can also increase user comfort by reducing pressure points or pressure lines running across the plantar surface of the foot. For instance, the convex portion 276 can distribute pressure away and/or throughout the lateral arch of the foot rather than overloading or concentrating pressure on one or more areas of the lateral arch via a discrete straight edge as in the prior art.

The configuration and dimensioning of the convex portion 276 can also help support the user's medial arch without the need of a separate or dedicated arch support. For instance, where a user has flat feet, the curvature of the convex portion 276 can contact and support the user's arch in an equinus position or the plantar-flexed position, taking pressure off the arch.

The shape of the convex portion 276 can be that of a partial arc of a circle. The partial arc can be defined at least in part by a central angle θ (in degrees) of the curve multiplied by a curve radius R (in length units) multiplied by (Π/180) as seen in FIG. 4. The length of the radius R can define the curvature of the convex portion 276. The central angle θ defines the length of the convex portion 276. The radius R and/or the central angle θ can therefore be customized for larger or smaller feet, users with flat feet or arched feet, or for other appropriate purposes. The radius R can be constant or variable. In an embodiment, the radius R can be larger to provide a smooth, comfortable shape.

It will be appreciated that the convex portion 276 can have other curved shapes, such as a portion of an ellipse or several arc portions, as long as the shape is at least in part generally convex to fit the curve of the foot and smooth enough to avoid pressure points and/or lines.

Optionally, the wedge section 256 can include a ramped edge 278 having a chamfered or beveled configuration at or near a front of the wedge section 256. The ramped edge 278 can generally face the toes. As seen, the ramped edge 278 can extend forwardly and downwardly from the convex portion 276 toward the forefoot region of the Achilles heel wedge 200. In an embodiment, the ramped edge 268 of the wedge section 254 can extend between the ramped edge 278 and the ramped edge 262 of the wedge section 252. In an embodiment, the ramped edge 268 can curve along the longitudinal axis A-A between the ramped edge 278 and the ramped edge 262 of the wedge section 252.

The ramped edge 278 can be configured to be positioned slightly distal to the heel or calcaneus or in any other suitable location. The ramped edge 278 can extend at an angle σ between the convex portion 276 and the bottom surface 270. The angle σ can be less than the angle β of the ramped edge 268, which, in turn, can result in a ramp length that is longer than the ramped edge 268. This ramp length can be actual or theoretical. The angle σ can be between about 5 degrees and about 15 degrees (e.g., about 10 degrees) relative to horizontal. It will be appreciated that the angle σ can be greater or less depending on the number and/or construction of the wedge sections, the desired treatment protocol, and/or other requirements.

The ramped edges 262, 268, 278 in combination can define a ramped surface of the Achilles heel wedge 200 extending from the convex portion 276. The angles or curvature of the ramped edge 262, 268, 278 can be different. This can allow the shape of the Achilles heel wedge 200 to better fit the shape of the foot, which, in turn, allows the wedge 200 to more naturally and/or comfortably support the foot. The angles of the ramped edge 262, 268, 278 can be configured so that the ramped surface generally approximates the curvature of the convex portion 276. For instance, the angle σ of the ramped edge 278 can be about 10 degrees relative to horizontal, the angle β of the ramped angle 268 can be about 20 degrees relative to horizontal, and the angle α can be about 30 degrees relative to horizontal. This advantageously forms a long, smooth curve-like shape along the top of the Achilles heel wedge 200, improving the fit and comfort of the Achilles heel wedge 200.

The angle σ of the ramped edge 278 can be less than the angle β of the ramped edge 268. The angle β of the ramped edge 268 can be less than the angle α of the ramped edge 262. The combination of the ramped edges and the curvature of the convex portion 276 can provide improved comfort over wedges in the prior art. Alternatively, the angle σ of the ramped edge 278 can be equal to or greater than the angle β of the ramped edge 268. The angle β of the ramped edge 268 can be equal to or greater than the angle α of the ramped edge 262.

The ramped surface and/or individual ramped edges can be formed during a molding process while forming the individual wedge sections. Alternatively, the ramped edges can be formed subsequent to a molding process using secondary grinding or cutting operations after the wedge sections have been attached to one another. While the ramped edges are described as being beveled or chamfered, it will be appreciated that the ramped edges may be curved or may exhibit any other suitable shape.

The distance between the posterior side of the wedge section 256 and the location where the convex portion 276 transitions to the ramped surface begins can be customized or selected to control the foot angle of the Achilles heel wedge 200. For instance, the convex portion 276 can end and the ramped surface can begin slightly in front of the heel or calcaneus. The ramped surface can end slightly behind the metatarsal heads on the forefoot. In other embodiments, the convex portion 276 can end and the ramped surface can begin in the mid-foot region or at a location behind the forefoot. The convex portion 276 can end and the ramped surface can begin at a location behind of the user's toes. Controlling this distance in combination with the configuration of the ramped surface and overall height of the wedge 200, allows the Achilles heel wedge 200 to customize or control the foot angle when the Achilles heel wedge 200 is being used, which, in turn, avoids foot angles that are too steep or abrupt to provide more comfortable support to the user's foot as discussed in more detail below.

The wedge section 256 can be designed to be removed from the Achilles heel wedge 200 and placed into typical footwear so that the wedge section 256, including its convex portion can be used for subsequent healing after a walker or other orthopedic device is no longer employed. The Achilles wedge 200 can be configured to be reused in whole or in part if one or more perforations are defined in the wedge section 256, creating a removable section on the wedge section 256.

As shown in FIG. 4, the individual wedge sections can include a thickness T defined between the top and bottom surfaces. The thickness T of the wedge sections corresponds to the desired incremental stretch length of the Achilles tendon, and may be any desired thickness T or height. For instance, the thickness T can be between about 1 mm and about 12 mm, between about 2 mm and about 10 mm, or between about 3 mm and about 9 mm. The thickness T of the wedge sections can vary along the length of the wedge sections. The thickness T and angle of ramped edge on each wedge section can define the length of the ramp on each wedge section. The greater that thickness T and the smaller the angle of the ramped edge, the longer the ramp formed by the ramped edge.

In use, the Achilles heel wedge 200 can be situated within the heel portion of an orthopedic device to shorten the Achilles tendon of a user to a first length. In order to incrementally stretch the Achilles tendon, the wedge sections can be removed from the Achilles heel wedge 200 to reduce the height of the Achilles heel wedge 200, thus stretching the Achilles tendon of the user to incrementally greater lengths.

To adjust the stretch length of the Achilles tendon at a first time, the Achilles heel wedge 200 can be removed from the heel portion of the orthopedic device. Then the wedge section 252 can be removed from the Achilles heel wedge 200, which can then be replaced in the orthopedic device. Treatment can then occur for the desired length of time to stretch the Achilles tendon at the length that is provided by removing the wedge section 252. This process can be repeated as necessary by removing subsequent wedge sections 254, 256 in succession to treat Achilles tendon injuries and/or assist in surgical recovery with incremental stretching of the Achilles tendon.

It should be noted that if greater height adjustment is needed during a specified treatment period, more than one of the wedge sections can be removed simultaneously. For instance, after an initial treatment period using the Achilles heel wedge 200 having wedge sections 252, 254, 256, the wedge sections 252 and 254 can be removed in order to provide a greater height adjustment to increase the amount that the Achilles tendon is stretched.

It should be appreciated that many variations of the wedge sections having different shapes and sizes can be used for stretching the Achilles tendon. Although such variations may differ in form, they perform substantially similar functions.

The thickness T of the individual wedge sections can be configured to fulfill requirements of specific therapeutic protocols where the foot must be placed in varying angles to achieve healing. For instance, each wedge section can have a thickness between about 7 mm and about 12 mm (e.g., about 10 mm). The thickness T of the individual wedge sections can be thinner (e.g., between about 2 mm and about 6 mm) to allow for the application of custom therapeutic protocols where the wedges are removed in response to a patient's progress during the course of therapy. It will be appreciated that the thickness T of the individual wedge sections can be more or less.

The Achilles heel wedge 200 can be configured to fit a specific size, or size range of orthopedic devices or feet. The Achilles heel wedge 200 can be made in extra-small/small, medium, and/or large/extra-large size, each size having the same or a selected foot angle. This has the effect of avoiding unwanted changes to the ratio of the foot angle that can result when the user is required to assemble a heel wedge from a range of differently sized wedges as in the prior art. For instance, one type of conventional heel wedge includes five wedge sections of varying lengths, each having a thickness of 10 mm. The heel wedge has only an angled ramped shape with steep angles, causing a user to feel unstable and applying additional stress on the foot. Further, if a user is wearing a size extra-large orthopedic device, the user inserts the three longest wedge sections into the orthopedic device. If a user is wearing a size small orthopedic device, the user inserts the three shortest wedge sections into the orthopedic device. Because the wedge sections have different lengths but the same thicknesses, the foot angle created by the smaller wedge sections is different than the foot angle created by the larger wedge sections, resulting in a lack of consistency in the heel/foot position.

In accordance with the disclosure, the arc length of the convex portion 276 or the distance from the heel of the wedge section 256 to where the most posterior ramped edge can be customized and/or selected based on the size of the Achilles heel wedge 200. This can allow the Achilles heel wedge 200 to position or control the angle of the foot in an equinus position. Thus, the Achilles heel wedge 200 can be made in different sizes while controlling the foot angle. For example, the Achilles heel wedge 200 in a small size can be configured to position the user's foot at about 15 degrees relative to horizontal or a support surface and the Achilles heel wedge 200 in a large size can be configured to position the user's foot at substantially the same angle. This avoids the steep angles present in the prior art that can cause users to feel unstable and/or provide undesired stress on the foot.

Figure 5:
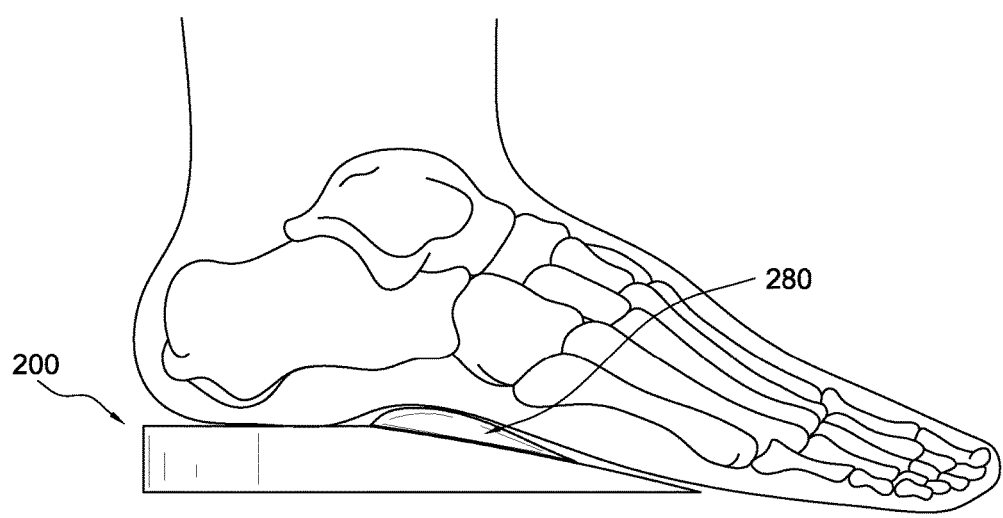
FIG. 5 is a side view of an Achilles heel wedge kit according to an embodiment.

In order to help secure the position of the foot, a separate arch support 280 can be attachable to the Achilles heel wedge 200. Referring to FIG. 5, the arch support 280 can be sized and configured to help maintain the position of the user's heel or calcaneus on the Achilles heel wedge 200, reducing the likelihood of the foot undesirably shifting or moving during use of the Achilles heel wedge 200. For instance, the arch support 280 can be attachable to the Achilles heel wedge 200 and configured to fit under the arch of the foot. The arch support 280 can have a length extending generally between about the calcaneal block and about the anterior end portion of the longitudinal arch of the foot.

The arch support 280 can also include a generally mound-shaped body having a width and a height. Such an arrangement advantageously provides a stop against forward and/or backward migration of the user's heel during use. The configuration of the arch support 280 also advantageously provides support to the user's medial arch so the lateral side of the foot is not unevenly supported (and therefore highly loaded).

Further, because the convex portion 276 of the Achilles heel wedge 200 can be configured to provide moderate support and an equinus position of the foot requires less arch support, the optional arch support 280 can have a lower profile shape than conventional arch supports. Alternatively, the body of the arch support 280 can have a generally triangular shape, a generally trapezium shape, a generally trapezoidal shape, combinations thereof, or the like.

Figure 6:
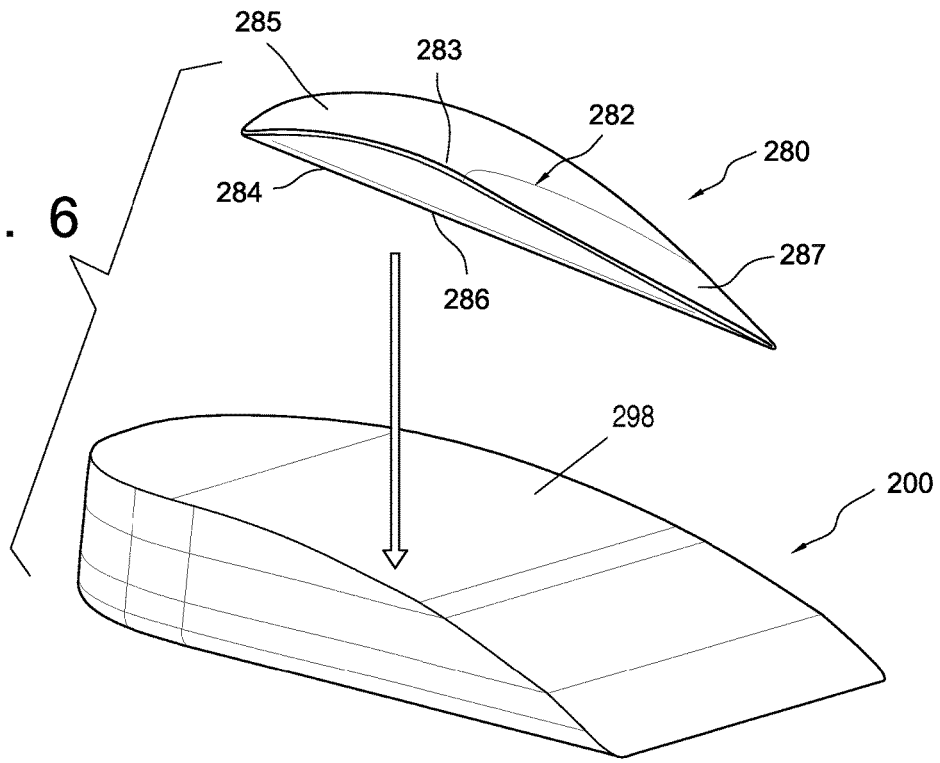
FIG. 6 is a partial exploded view of the Achilles heel wedge kit shown in FIG. 5.
Figure 7:
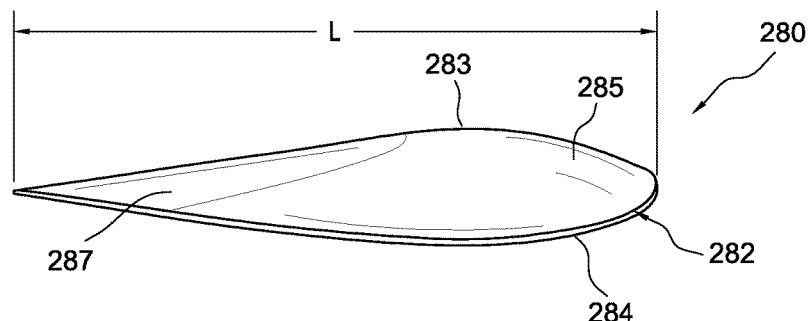
FIG. 7 is an isometric view of the arch support shown in FIG. 5.

The construction of the arch support 280 will now be discussed in greater detail in connection with FIGS. 6 and 7. The arch support 280 can be formed, for example, from EVA foam, vinyl nitrile foam, combinations thereof, or any other suitable material. The arch support 280 can be configured to provide more cushioning than the wedge sections 252, 254, 256. For example, the arch support 280 can include an 8-10# EVA foam and the wedge sections can include a 12-14# EVA foam. The arch support 280 can include a 6# EVA foam compression molded to yield stiffness of about an #8 EVA foam and the wedge sections can include a 14# polyethylene foam. The arch support 280 can include an 8# vinyl nitrile foam and the wedge sections can include a 10# vinyl nitrile foam.

The arch support 280 can also include one or more materials allowing the bottom surface of the arch support 280 to substantially conform to the upper surface 298 of the Achilles heel wedge 200. The arch support 280 can be formed of softer materials than the wedge sections. This beneficially makes the arch support 280 more comfortable under the medial arch, as the medial arch does not have fat pads and is thus more sensitive than the heel or the forefoot of the foot.

As seen, an upper surface 282 of the arch support 280 can be contoured to fit under the medial arch of the user's foot. The upper surface 282 can include a peak 283 defined as the uppermost extending portion of the arch support 280, a posterior curvilinear section 285 extending from the peak 283 to the upper surface 298 of the Achilles heel wedge 200, and an anterior curvilinear section 287 extending from the peak 283 toward the forefoot and the upper surface 298 of the Achilles heel wedge 200. A medial side of the arch support 280 can include a generally planar wall 286 extending between the posterior section 285 and the anterior section 287. A lateral side of the arch support 280 can gradually taper from the peak 283 toward the upper surface 298 of the Achilles heel wedge 200. The anterior section 287 of the arch support 280 can taper gradually toward the forefoot from the peak 283. A lower surface 284 of the arch support 280 can be attachable to the upper surface 298 of the Achilles heel wedge 200.

The arch support 280 can extend axially along the longitudinal axis A-A (shown in FIG. 4), having a length L, with the anterior section 287 being relatively longer than the posterior section 285. The arch support 280 can also include a width defined between the medial and lateral sides. The length L of the arch support 280 can be greater than the width of the arch support 280. It will be appreciated that the length and/or generally shape of the arch support 280 can be customized based on the anatomical features of the user's foot.

The arch support 280 can be glued with adhesive directly to the upper surface 298 of the Achilles heel wedge 200. The arch support 280 can be secured with double sided tape or a hook-and-loop type system to the upper surface 298 of the Achilles heel wedge 200. Alternatively, the arch support 280 may be held in place on the upper surface 298 of the Achilles heel wedge 200 by the weight of the user and frictional forces. Further, the separate arch support 280 can allow the arch support 280 to be placed in a certain position for specific users or omitted if the arch support is deemed unnecessary.

It should be appreciated that many variations of the arch support 280 having different shapes and sizes can be used for supporting the user's arch and maintaining the position of the user's heel on the Achilles heel wedge 200. Although such variations may differ in form, they perform substantially similar functions.

Figure 8:
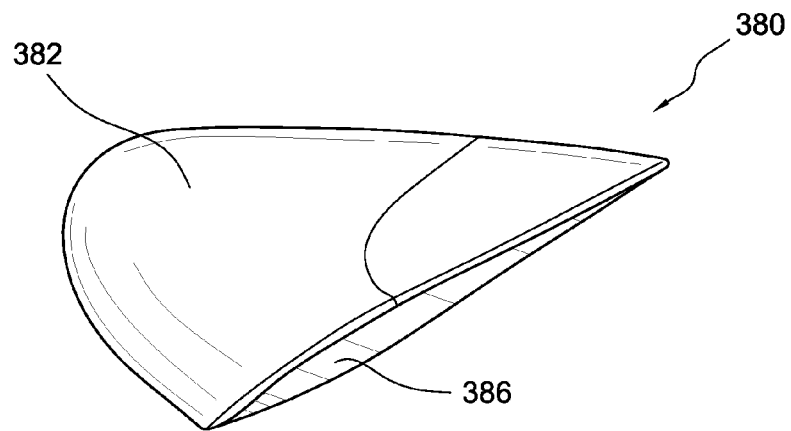
FIG. 8 is an isometric view of an arch support according to another embodiment.
Figure 9:
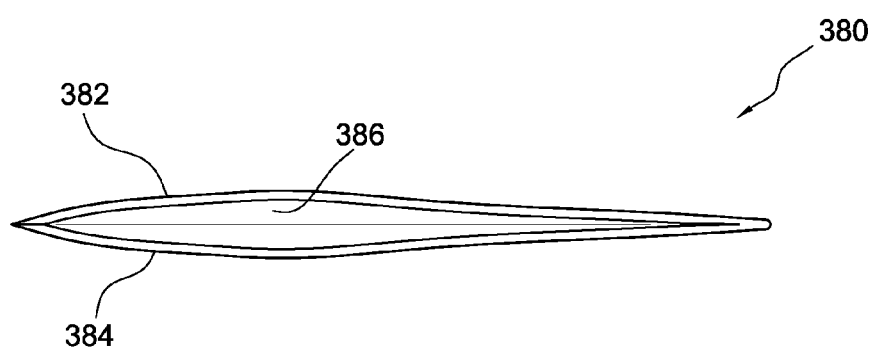
FIG. 9 is a side view of the arch support shown in FIG. 8.
Figure 10:
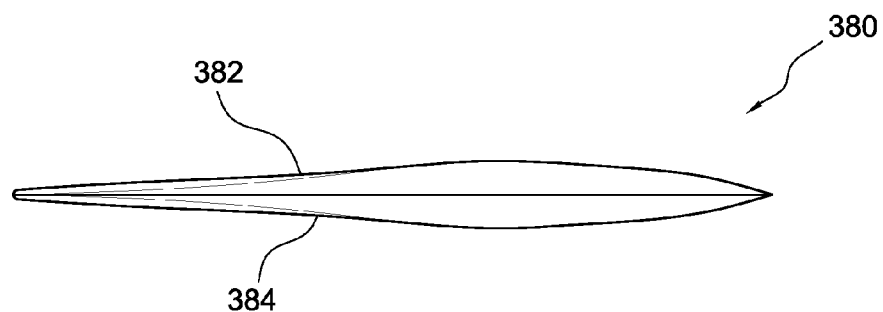
FIG. 10 is another side view of the arch support shown in FIG. 8.

It should be further appreciated that the arch support 280 can be formed to be situated at the proper location under either a right foot or a left foot. The arch support can also be configured so that the same arch support can be used on the left or right foot. For instance, FIGS. 8-10 illustrate an arch support according to another embodiment comprising a universal arch support 380 including an upper surface 382 and a lower surface 384 that are substantially horizontally symmetric, both surfaces being contoured to fit under the arch of the foot.

As seen, the contour of the lower surface 384 can be substantially a mirror image of contour of the upper surface 382. This advantageously allows the same arch support to be used on the left or right foot by simply turning the arch support 380 over. Such a configuration can allow a user to position the generally planar wall 386 of the arch support 280 on the same side of the Achilles heel wedge as the medial side of the foot and to reverse the vertical position of the upper and lower surfaces (e.g., the lower surface 384 can be positioned to fit under the arch of the foot and the upper surface 386 can be positioned to form the bottom of the arch support 380) as needed.

Figure 11:
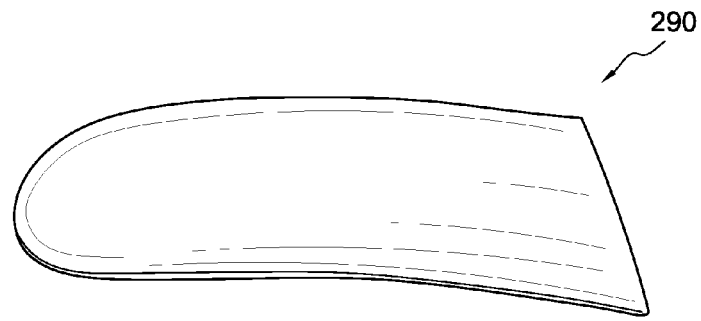
FIG. 11 is a foot surface cover according to an embodiment.
Figure 12:
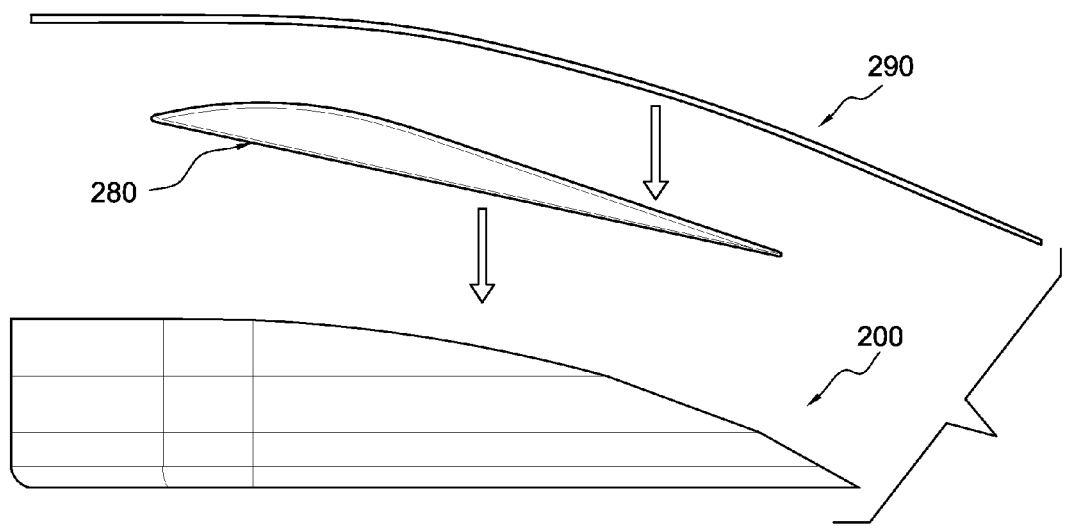
FIG. 12 is a partial exploded view of Achilles heel wedge kit according to another embodiment.

Optionally, the Achilles heel wedge 200 can include a foot surface cover 290 configured to cover both the wedge sections and the arch support 280 as shown in FIGS. 11 and 12. The foot surface cover 290 can provide cushioning. The foot surface cover 290 can also distribute pressure over a larger area, which, in turn, can limit pressure points. The foot surface cover 290 can also allow for some small amount of movement of the Achilles tendon. Such small amounts of movement can better align tendon fibers during healing, resulting in a stronger Achilles tendon than complete immobilization wherein the tendon fibers may heal randomly.

The foot surface cover 290 can include any suitable material. For instance, the foot surface cover 290 can be formed, for example, from cork, foam, combinations thereof, or any other suitable material. The foot surface cover 290 can be made from a material that is softer than the arch support 280 and/or the wedge sections. The foot surface cover 290 can be soft, resilient, and can exhibit a higher coefficient of friction, which, in turn, prevents the foot from shifting or moving during use.

The foot surface cover 290 can be formed from a #6 EVA foam. The foot surface cover 290 can be formed from an 8# vinyl nitrile. In some embodiments, a liner may be associated with an orthopedic device (e.g., walker 100 or 110). The liner can at least in part receive the user's foot and is positionable over the wedge sections (and optionally the arch support 280). Similar to the foot surface cover 290, the liner can provide cushioning and/or allow for a small amount of movement of the Achilles tendon.

The Achilles heel wedge 200 can be sold in an Achilles heel wedge kit. For example, a clinician can buy an orthopedic device and then buy an Achilles heel wedge kit that is sized to fit the orthopedic device and/or the patient's foot. If the patient does not need an arch support, the clinician may choose not to purchase an arch support. If the patient requires a more granulated treatment protocol, the clinician may purchase an Achilles heel wedge kit including a greater number of thinner wedge sections. If a patient requires less stretching of the Achilles tendon, the clinician may purchase an Achilles heel wedge kit including an Achilles heel wedge having a lower overall height.

Figure 13:
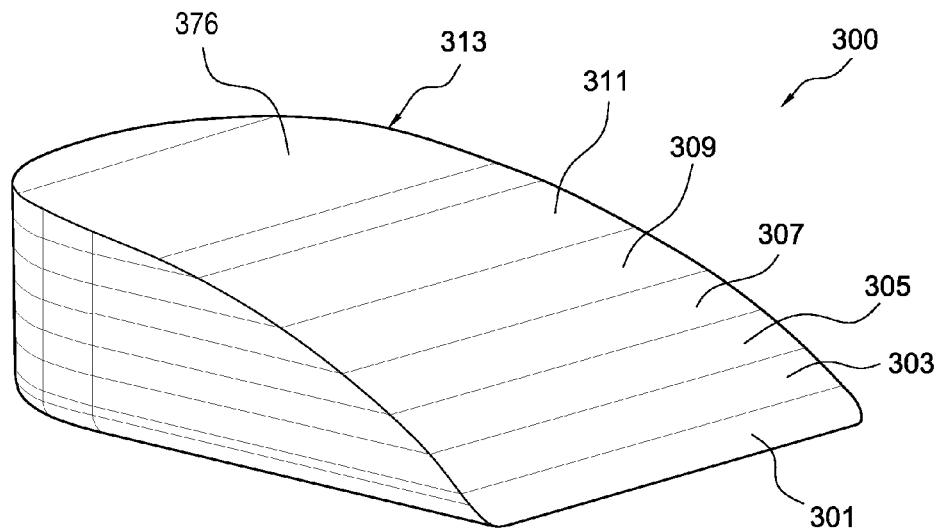
FIG. 13 is an isometric view of an Achilles heel wedge according to another embodiment.
Figure 14:
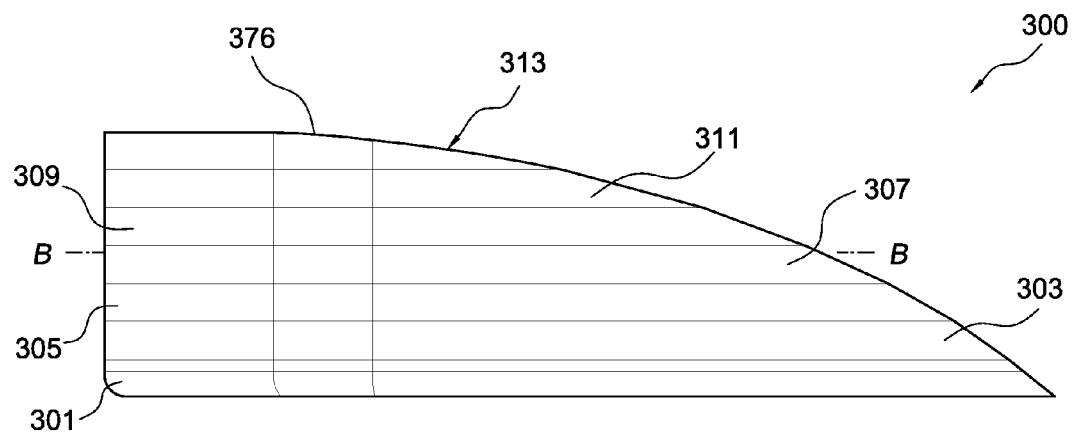
FIG. 14 is a side view of the Achilles heel wedge shown in FIG. 13.

The Achilles heel wedge 200 is shown comprising three wedge sections. However, the number of wedge sections shown is merely exemplary, and any suitable number of wedge sections may be used in order to achieve the desired amount and increments of height adjustments. For example, FIGS. 13 and 14 illustrate an exemplary embodiment of an Achilles heel wedge 300 including wedge sections 301, 303, 305, 307, 309, 311, and 313. The Achilles heel wedge 300 can define a longitudinal axis B-B.

The wedge section 301 can be longer than the wedge section 303. The wedge section 303 can be longer than the wedge section 305. The wedge section 305 can be longer than the wedge section 307. The wedge section 307 can be longer than the wedge section 309. The wedge section 309 can be longer than the wedge section 311. The wedge section 311 can be longer than the wedge section 313.

The wedge sections 301, 303, 305, 307, 309, 311 can have generally or substantially parallel top and bottom surfaces with a chamfered, curved, or beveled ramped edge on or toward the front side of the wedge section facing the toes. The wedge section 313 can include a convex portion 376 extending in a longitudinal direction along the longitudinal axis B-B. The convex portion 376 is sized and configured to smoothly and comfortably support the foot. The convex portion 376 within the natural curve of the foot can relieve pressure off the foot and the tendons and ligaments that support the foot.

The ramped edges of the bottom wedge sections can in combination form a ramped surface of the Achilles heel wedge 300. The individual ramped edges can be angled so that the ramped surface generally approximates the curvature of the convex portion 376 as best seen in FIG. 14. For instance, the angle of the ramped edge of the wedge section 301 can be about 40 degrees relative to horizontal. The angle of the ramped edge of the wedge section 303 can be about 35 degrees relative to horizontal. The angle of the ramped edge of the wedge section 305 can be about 30 degrees relative to horizontal. The angle of the ramped edge of the wedge section 307 can be about 25 degrees relative to horizontal. The angle of the ramped edge of the wedge section 309 can be about 20 degrees relative to horizontal. The angle of the ramped edge of the wedge section 311 can be about 15 degrees relative to horizontal. The angle of the ramped edge of the wedge section 313 can be about 10 degrees relative to horizontal. It will be appreciated that the angles of the ramped edges can be greater or less depending on the number of wedge sections and/or the thickness of the individual sections.

The ramped edges and the curvature of the convex portion 376 can be customized to better fit the natural curve of the user's foot. As seen, the thickness T of the individual wedge sections can be relatively thinner (e.g., between about 2 mm and about 6 mm). This can allow for more customization or granularity.

It will be appreciated that the embodiments of the Achilles heel wedge are to be regarded as exemplary only. For example, the Achilles heel wedge can be a single wedge with partial cuts to differentiate each wedge section. Examples of an Achilles heel wedge and method for making the same are found in U.S. patent application Ser. Nos. 13/173,496 and 14/457,553, the disclosure of which is incorporated herein by reference in its entirety. In other embodiments, the different wedge sections may be formed from different materials. In yet other embodiments, the different wedge sections may vary in density. For example, the topmost wedge section may have a greater density than the bottommost wedge section or the density of the Achilles heel wedge may decrease from top to bottom, increasing the useful life of the Achilles heel wedge.

Figure 15:
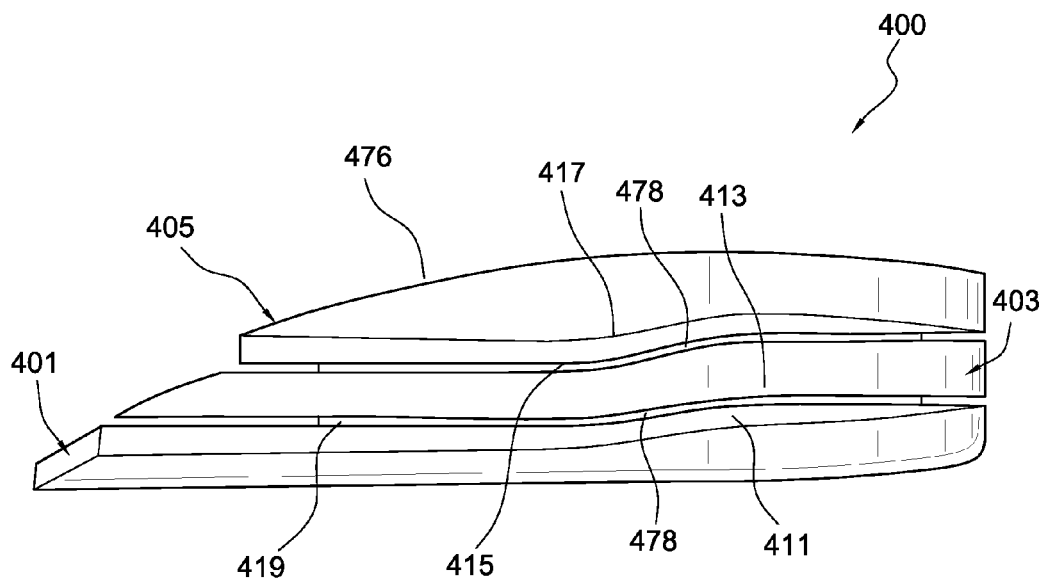
FIG. 15 is a side view of an Achilles heel wedge according to another embodiment.
Figure 16:
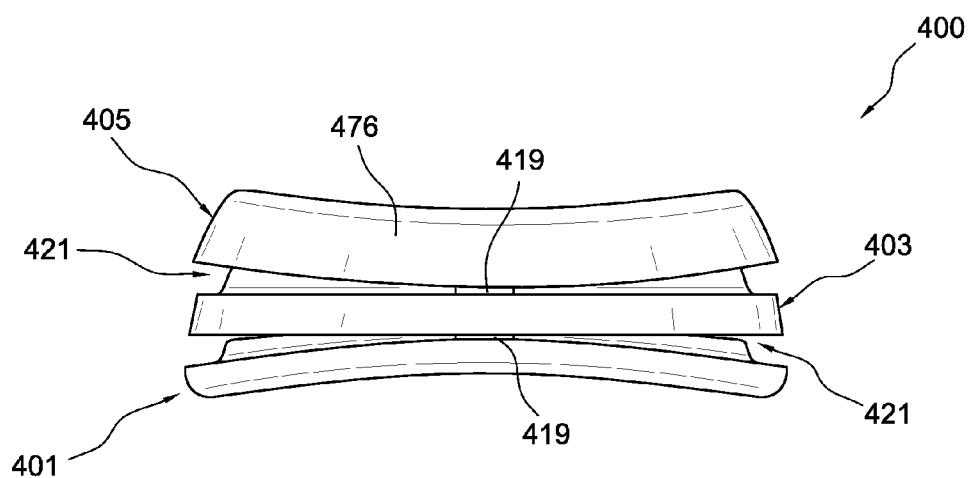
FIG. 16 is a front view of the Achilles heel wedge shown in FIG. 15.

FIGS. 15 and 16 illustrate an exemplary embodiment of an Achilles heel wedge 400 according to another embodiment. The Achilles heel wedge 400 includes wedge sections 401, 403, and 405. Wedge section 405 includes a convex portion 476 on the top surface thereof. The wedge section 401 includes a top surface 411 and the wedge section 403 includes a bottom surface 413 shaped and configured to interface with the top surface 411 of the wedge section 401. The wedge section 405 can include a bottom surface 417 shaped and configured to interface with the top surface 415 of the wedge section 403.

As seen, the Achilles heel wedge 400 can have contoured interface portions 478 between each of the wedge sections. The contoured interface portions 478 are adapted for helping the Achilles heel wedge 400 provide or maintain arch support when one or more of the wedge sections are removed from the Achilles heel wedge 400. For instance, when the wedge sections 401, 403 are removed, the user's foot typically moves toward neutral, which, in turn, causes the user's foot and/or Achilles heel wedge 400 to flatten out.

The contoured interface portions 478 are shaped and positioned such that when one or more of the wedge sections are removed from the Achilles heel wedge 400 the contoured interface portions 478 raise the convex portion 476 relative to the user's longitudinal arch. This beneficially reduces the dorsiflexion of the foot, which, in turn, maintains contact and support the user's longitudinal arch even as the foot moves toward the neutral position. This can also help the top surface of the heel wedge 405 support a separate arch support in an appropriate position relative to the plantar aspect of the foot as the foot moves toward the neutral position.

As best shown in FIG. 16, the Achilles heel wedge 400 can further include at least one central support 419 formed between the wedge sections. The central support 419 can extend longitudinally at least in part between the back and front parts of the heel wedge 400. The central support 419 can have a width that is substantially less than the width of the wedge sections such that slits or open channels 421 are formed between the wedge sections on either side of the central support 419. The slits or open channels 421 define a height between adjacent wedge sections that increases in a direction extending away from the central support 419. The central support 419 can be formed from the same material as the wedge sections or the central support 419 can be formed from different materials.

The central supports 419 can integrally attach the wedge sections to one another so that the Achilles heel wedge 400 comprises a single member. This can help keep the wedge sections together when the Achilles heel wedge 400 is not being used so as to not be so easily misplaced. This can also help keep the wedge sections in better alignment during use.

The central support 419 can provide a guide or seam along which a user can tear, cut, or rip one or more wedge sections from the Achilles heel wedge 400. This has the effect of reducing the likelihood of the wedge sections tearing or physically separating in undesirable locations and/or directions when being removed by a user, which, in turn, makes the Achilles heel wedge 400 easier to use. Alternatively, the central support 419 can include a sharp edge, making the central support 419 easier to tear or rip.

While various aspects and embodiments have been disclosed herein, other aspects and embodiments are contemplated. For example, while the curved portion of the topmost wedge section is described extending in a longitudinal direction, in other embodiments, it can extend laterally and/or medially relative to the longitudinal axis of the Achilles heel wedge. In other embodiments, the wedge sections can include top and bottom surfaces that are generally non-parallel. While the front edge of the Achilles heel wedge is shown being generally planar, in other embodiments, the front edge of the Achilles heel wedge can be curved or may include any other suitable shape.

The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. An Achilles heel wedge comprising: a back part; a front part;
    a longitudinal axis extending in a longitudinal direction between the back part and the front part;
    a first wedge section defining a bottom surface, and a top surface forming a convex portion curving along the longitudinal axis and extending between side portions of the first wedge section, the convex portion is positionable under a longitudinal arch of a foot of a user during use;
    a second wedge section removably attachable to the bottom surface of the first wedge section, the second wedge section defining parallel top and bottom surfaces, and a ramped edge at or near a front of the second wedge section, the ramped edge extending downwardly and forwardly relative to the first wedge section and the top surface of the second wedge section;
    a central support formed between and integrally attaching the first and second wedge sections to form a single member, the central support extending longitudinally between the back and front parts and providing a guide along which a user can tear the first wedge section from the second wedge section; and
    at least one longitudinal slit defined between the first and second wedge sections and the central support, wherein the at least one longitudinal slit defines a distance between the first and second wedge sections that increases as the at least one longitudinal slit extends away from the central support in a transverse direction that extends through a medial side and a lateral side of the heel wedge.

2. The Achilles heel wedge of claim 1, wherein the top surface of the first wedge section further defines a generally planar portion extending rearwardly from the convex portion.

3. The Achilles heel wedge of claim 1, wherein the second wedge section is longer than the first wedge section.

4. The Achilles heel wedge of claim 1, wherein the ramped edge of the second wedge section extends forwardly and downwardly from a ramped edge of the first wedge section.

5. The Achilles heel wedge of claim 1, wherein the convex portion has an arc length dimensioned relative to an overall length of the Achilles heel wedge to position the foot of the user in an equinus position.

6. The Achilles heel wedge of claim 1, further comprising a separate arch support attachable to an upper surface of the Achilles heel wedge, the arch support having a contoured, elongate configuration extending substantially between the heel and forefoot of the user.

7. The Achilles heel wedge of claim 6, wherein the arch support has a length dimensioned to extend between about a calcaneal block and about an anterior end portion of the longitudinal arch of the user.

8. An orthopedic system comprising:
    an orthopedic device defining a heel portion; and
    an Achilles heel wedge positionable within the heel portion of the orthopedic device, the Achilles heel wedge comprising:
    a back part;
    a front part;
    a longitudinal axis extending in a longitudinal direction between the back part and the front part;
    a first wedge section defining a bottom surface, and a top surface forming a convex portion curving along the longitudinal axis and extending between side portions of the first wedge section, the convex portion is positionable under a longitudinal arch of a foot of a user during use;
    a second wedge section removably attachable to the bottom surface of the first wedge section, the second wedge section defining substantially parallel top and bottom surfaces, and a ramped edge at or near a front of the second wedge section, the ramped edge extending downwardly and forwardly relative to the first wedge section and the top surface of the second wedge section;
    a central support formed between and integrally attaching the first and second wedge sections to form a single member, the central support extending longitudinally between the back and front parts and providing a guide along which a user can tear the first wedge section from the second wedge section; and
    at least one longitudinal slit defined between the first and second wedge sections and the central support, wherein the at least one longitudinal slit defines a distance between the first and second wedge sections that increases as the at least one longitudinal slit extends away from the central support in a transverse direction that extends through a medial side and a lateral side of the heel wedge.

9. The system of claim 8, wherein the first wedge section defines a ramped edge extending downwardly and forwardly from the convex portion.

10. The system of claim 9, wherein the ramped edge of the second wedge section extends forwardly and downwardly from the ramped edge of the first wedge section.

* * * * *